United States Patent

Groux

[19]

[11] Patent Number: 5,913,836
[45] Date of Patent: Jun. 22, 1999

[54] BODY TONING METHOD AND APPARATUS

[75] Inventor: Paul D. Groux, Vallejo, Calif.

[73] Assignee: Allied Health Association, Inc., Englewood, Colo.

[21] Appl. No.: 08/803,500

[22] Filed: Feb. 20, 1997

Related U.S. Application Data

[60] Provisional application No. 60/011,903, Feb. 20, 1996, abandoned.

[51] Int. Cl.$^6$ ........................................... A61N 1/36
[52] U.S. Cl. .................................... 601/21; 607/3
[58] Field of Search ................................ 601/15, 21, 133; 607/3, 76, 150

[56] References Cited

U.S. PATENT DOCUMENTS

| 861,349 | 7/1907 | Beaubien . |
| 1,379,919 | 5/1921 | Herndon ..................................... 601/21 |
| 1,534,444 | 4/1925 | Feldheym . |
| 1,811,764 | 6/1931 | Sherwood . |
| 1,948,067 | 2/1934 | De Carreno et al. . |
| 2,480,029 | 8/1949 | Jozsy . |
| 2,959,167 | 11/1960 | Leclabart . |
| 3,872,859 | 3/1975 | Pitzen et al. . |
| 4,175,551 | 11/1979 | D'Haenens et al. . |
| 4,249,534 | 2/1981 | Muldrow, Jr. ............................ 601/133 |
| 5,484,387 | 1/1996 | Pitzen . |
| 5,484,390 | 1/1996 | Chiang ..................................... 601/133 |

FOREIGN PATENT DOCUMENTS

| 2 484 262 | 3/1980 | France . |
| 2040 181 | 8/1970 | Germany . |
| 150643 | 9/1920 | United Kingdom . |

*Primary Examiner*—William E. Kamm
*Attorney, Agent, or Firm*—Brian D. Smith, P.C.

[57] ABSTRACT

Method and apparatus are disclosed for body toning which includes the reduction of total body fat content. The method includes squeezing a fatty area of an individual's body with an energized pair of electrodes or probes so as to pass an electrical signal through the fatty area which is sufficient to rupture or break down fat cells in the fatty area. The electrical signal is set so that it has a frequency preferably between 15 and 60 Hz and a current between about 2000 and 3600 micro amperes. The squeezing technique is preferably followed with a technique referred to as gliding. Gliding involves adjusting the energization of the probes so that they preferably generate a signal having a frequency of between about 125 and 600 Hz and a current of between about 1600 and 2400 microamps. The probes are then moved slowly, actually glided, in spaced unison over the previously treated area in a fashion which is believed to push or facilitate absorption of the fat cell contents into the body fluid where it is ultimately excreted from the body.

22 Claims, 4 Drawing Sheets

BODY TONING METHOD AND APPARATUS

CROSS REFERENCE TO RELATED APPLICATIONS

This application is a nonprovisional application claiming the benefit under 35 USC 119(e) of U.S. provisional application Ser. No. 60/011,903, filed on Feb. 20, 1996, now abandoned.

TECHNICAL FIELD OF THE INVENTION

The invention pertains generally to method and apparatus for body toning and, more particularly, to methods and apparatus for toning muscle and reducing body fat.

BACKGROUND OF THE INVENTION

The desire of mankind to reduce body fat and improve muscle tone is relentless as demonstrated by the fact that one cannot watch television very long today without viewing a commercial advertising a low fat or low calorie food or beverage, or some type of exercise equipment or exercise videotape.

Almost all of the exercise equipment commercials claim that their particular device is superior in either exercising certain muscles or in providing a thorough workout with the least possible effort. Some commercials even claim that the use of their device or machine will reduce body fat and result in weight loss without any effort by the user.

While use of some of these devices may yield their claimed results, those not requiring any exertion or effort by the user are not believed to work. Thus, there remains a need and certainly a desire for apparatus and methods which will in fact improve muscle tone and reduce body fat without requiring any exertion by the user.

DISCLOSURE OF THE INVENTION

The present invention provides a method and apparatus for toning an individual's body, and is specifically directed to method and apparatus for improving muscle tone and reducing total body fat content. In its broadest sense, the body toning method of the present invention is directed to squeezing a fatty area of an individual's body with an energized pair of electrodes or probes so as to pass an electrical signal through the fatty area which is sufficient to rupture or break down fat cells in the fatty area. The contents of the ruptured or broken down fat cells are then excreted from the body to reduce one's total body fat content.

The electrical signal passing between the probes through the subject's fatty area while this area is squeezed with the probes is set so that it has a frequency preferably between 15 and 60 Hz and a current between about 2000 and 3600 micro amperes.

To enhance fat reduction, the foregoing step of squeezing the fatty area with the probes is preferably immediately followed with a technique referred to as gliding which is believed to facilitate absorption of the ruptured or released fat cell contents into the body's fluid, where it is ultimately excreted from the body.

Gliding involves adjusting the energization of the probes so that they preferably generate a signal having a frequency of between about 125 and 600 Hz and a current of between about 1600 and 2400 microamps which is typically lower than the current applied during the squeezing step. The probes are then moved slowly, actually glided, in spaced unison over the previously treated area in a fashion which is believed to push or facilitate absorption of the fat cell contents into the body fluid as previously indicated.

In a preferred embodiment, the probes or electrodes are also mechanically vibrated as they are used to carry out the aforementioned fat reduction and gliding steps. Mechanical vibration is particularly useful during the fat implosion step in that it masks the electrical sensation often associated with higher currents. The electrodes may also be heated during these steps which also makes the treatment more comfortable.

In another preferred embodiment of the present invention, the foregoing fat implosion and gliding steps are preceded by a muscle toning step in which the muscle in the area to be treated is first toned, i.e. relaxed and/or tightened. This step involves movement of the energized probes along the muscle to be treated. Movement of the probes away from each other along the length of the muscle causes the muscle to relax. Movement of the probes towards each other along the length of the muscle causes the muscle to tighten. The electrical signal passing between the probes is also preferably adjusted so that it has a frequency of between about 0.6 and 325 Hz and a current of between 1800 and 3200 microamps. The process is also repeated on immediately adjacent areas of the muscle until the entire muscle is treated.

The foregoing treatment, preferably all three of the above-described steps, is repeated twice a week for at least three weeks, or until satisfactory results are obtained.

With some individuals it may be beneficial to occasionally adjust the current, polarity and frequency of the signal to prevent the muscle or fatty tissue from acclimating or habitualizing to any frequently used signal.

BRIEF DESCRIPTION OF THE DRAWINGS

The invention will be more readily understood by reference to the accompanying drawings wherein like reference numerals indicate like elements throughout the drawing figures, and in which.

DETAILED DESCRIPTION OF PREFERRED EMBODIMENTS

Figure 1:
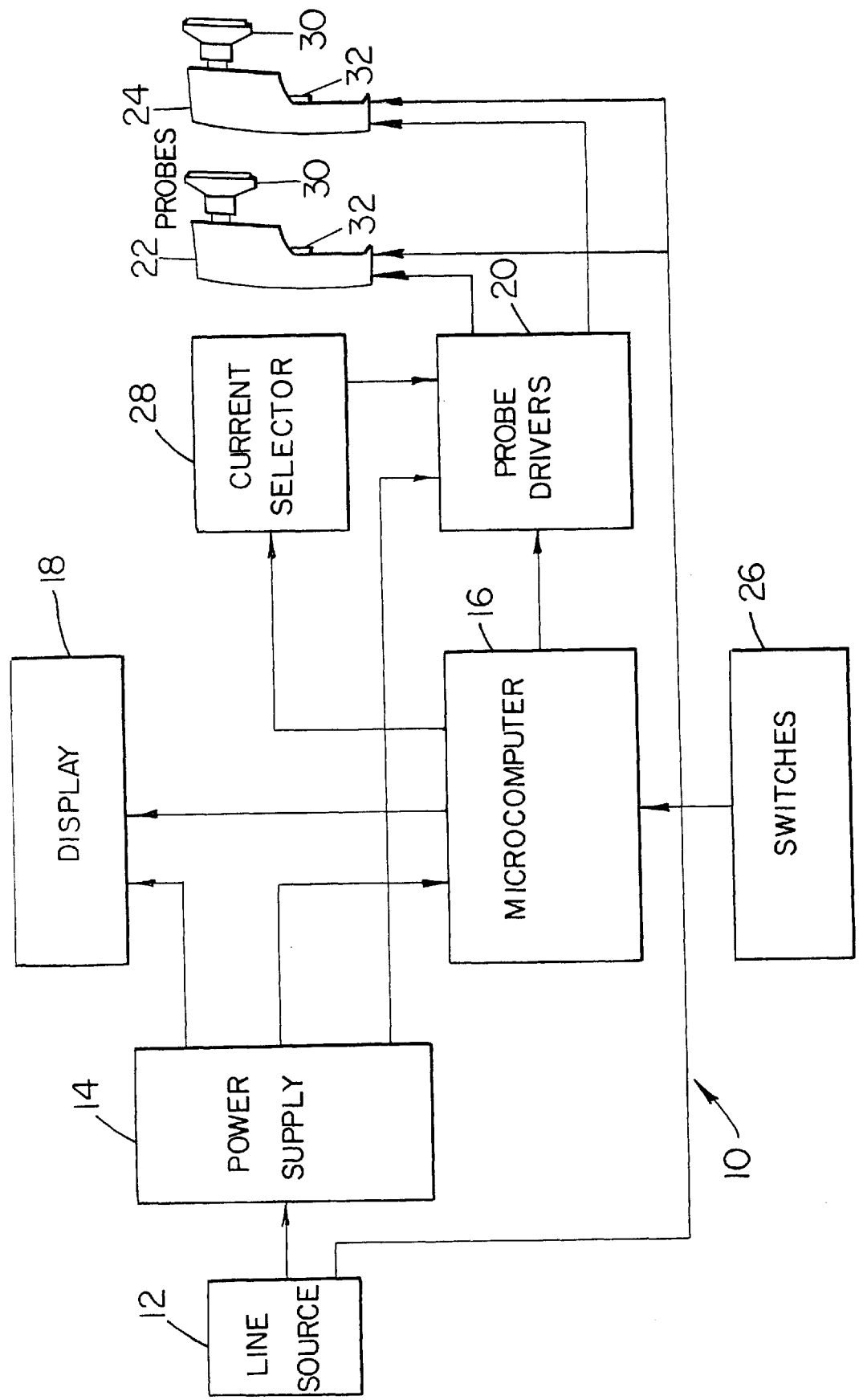
FIG. 1 is a block diagram of an apparatus constructed in accordance with a preferred embodiment of the invention.

As indicated in FIG. 1, the system which is referred to generally as desktop unit 10 is powered by a 120 volt source referred to as line source 12. Line source 12 is connected to a power supply circuit 14 which supplies power to the unit's microcomputer circuit 16, display circuit 18 as well as the unit's probe driver circuit 20 which is connected to probes 22, 24, as such is described in more detail below with respect to FIGS. 2 and 2A. Line source 12 also supplies power directly to the probes to operate a vibrator (not shown) contained within each probe.

Push-button switches (identified generally by numeral 26 in FIG. 1) connected to microcomputer 16 allow the operator to select the current intensity, frequency and polarity of the signal supplied to the probes and in addition allows the operator to turn the microcomputer on or off by putting the microcomputer in an awake or sleep state, as more fully described below.

The apparatus of the preferred embodiment will now be described in greater detail with reference to the electronic circuit diagram of FIGS. 2 and 2A.

Power for the unit is supplied by line source 12 at 120 volts RMS (Root Mean Square) which is controlled by on/off power switch S1. When being supplied to unit 10, power flows through fuse F1 to two transformers T1 and T2, through the connecting wires to the probes and through switch S2 to transformer T3. The voltage from transformer T3 is drooped by potentiometers P1a and P1b and is supplied to heaters (not shown) contained inside each probe. Additional switches contained in the probes turn a vibrator (not shown) contained inside each probe on or off.

The voltage from transformer T2 is rectified by rectifiers D2 and D3 and filtered by capacitor C3 to supply approximately positive 55 volts direct current to the voltage regulator U2. The voltage from transformer T2 is also rectified by rectifiers D4 and D5 and filtered by capacitor C5 to supply approximately negative 55 volts direct current to the voltage rectifier U3. These regulators drop the voltage to positive and negative 45 volts respectively to supply the probe driver circuit. Capacitors C4 and C6 are used to stabilize the voltage regulators U2 and U3.

The voltage from transformer T1 is rectified by bridge rectifier D1 and filtered by capacitor C1 to supply approximately 17 volts direct current to the voltage regulator U1. This regulator drops the voltage to 5 volts to supply the microcomputer circuit. Capacitor C2 is used to stabilize the voltage regulator U1.

The probe driver 20 as identified in FIG. 1 consists of operational amplifier U8 and U6b. Amplifier U8 is a high voltage operational amplifier and is configured as a modified "Howland" circuit to provide bipolar constant current to the probes. Because of the wide range specified for the initial offset voltage on amplifier U8 a second amplifier U6b has been added to the circuit. This is a lower voltage unit and, in conjunction with amplifier U8, acts as a single operational amplifier. Looking at the amplifier circuit as described above, the resistors R35 through R39 are proportioned to provide a positive output of 3000 micro amperes per volt of input on resistor R36 or a negative output of 3000 micro amperes per volt of input on resistor R35. The remaining parts R43, R44, R45, C9 and C10 are frequency compensation components for the operational amplifier U8. Resistors R30 and R46 are for circuit calibration.

Current selector 28 as identified in FIG. 1 consists of resistors R21 through R27, R29, R30 and R32 along with operational amplifier U6 and its resistors R28 and R31. These components form a programmed precision voltage source for the probe driver. The left ends of resistors R21 through R27 connect to outputs from one register of the microcomputer. These points in the circuit are normally held at ground potential by the microcomputer 16 and are raised to a 5 volt level to select the output current. For example, raising the register output to resistor R22 provides a voltage of approximately 0.333 volts through one of the analog switches U7a to resistor R35 or U7b to resistor R36, thus programming the probe output to 1000 micro amperes. The output current provided to the probe is the sum of all the lines selected, or raised. For example, raising the register outputs to resistors R22 and R23 provides a voltage of approximately 0.6 volts to resistor R35 or R36, thus programming the probe output to 1800 micro amperes.

The current selector 28 is connected to the probe driver 20 by analog switches U7a through U7d. To pass positive current from one probe to the other through a skin load, analog switches U7b and U7c are turned on. Switch U7b connects resistor R36 on the probe driver operational amplifier U8 to the current selector voltage output and switch U7c is used to clamp resistor R35 to ground potential. Similarly, to pass negative current from one probe to the other through a skin load, analog switches U7a and U7d are turned on. Switch U7a connects resistor R36 on the probe driver operational amplifier U8 to the current selector voltage output and switch U7d is used to clamp resistor R35 to ground potential. The analog switch control inputs are connected to the microcomputer 16 (identified as U3 in FIG. 2) so that the output polarity can be selected by the microcomputer by dropping one line at a time. For a single polarity only one line is dropped and raised while bipolar output requires that both lines be alternately dropped and raised. The logic inverter U5a causes the analog switch pair, U7a and U7c, to act as a SPDT (single pole, double-throw) switch while inverter U5b acts in a similar fashion for analog switches U7b and U7d. Resistor R5 and light emitting diodes D6 and D7 provide a front panel indication of the immediate output signal polarity to the operator.

Probe 22 is connected through fuse F3 to the junction of resistors R38 and R39. The second probe 24 is connected through fuse F2 to ground. Fuses F21 and F3 are low current fuses which provide protection to the patient if a fault occurs in the circuit.

Since the method of the present invention requires the ability to produce a maximum output of positive and negative 3400 micro amperes into a skin resistance loading of 10,000 ohms, this dictates that a minimum of 34 volts of each polarity be supplied to the probe. Adding this value to the voltage drop inherent in the circuit requires a bipolar supply voltage of approximately 45 volts even when the line voltage drops to 110 volts RMS. This voltage is supplied by the power supply.

Figure 2:
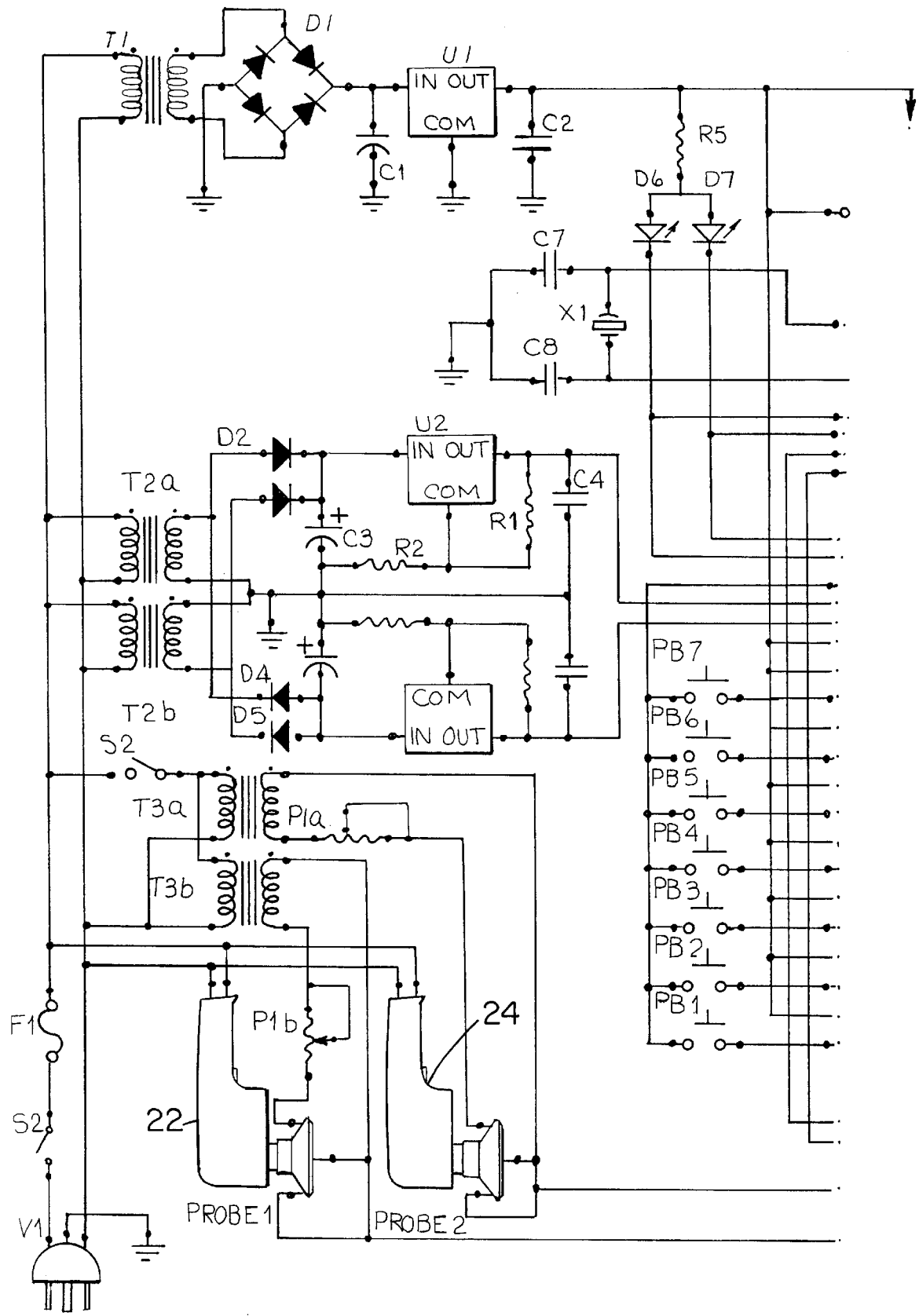
FIGS. 2 and 2A are an electronic circuit schematic diagram of the apparatus of FIG. 1.
Figure 2A:
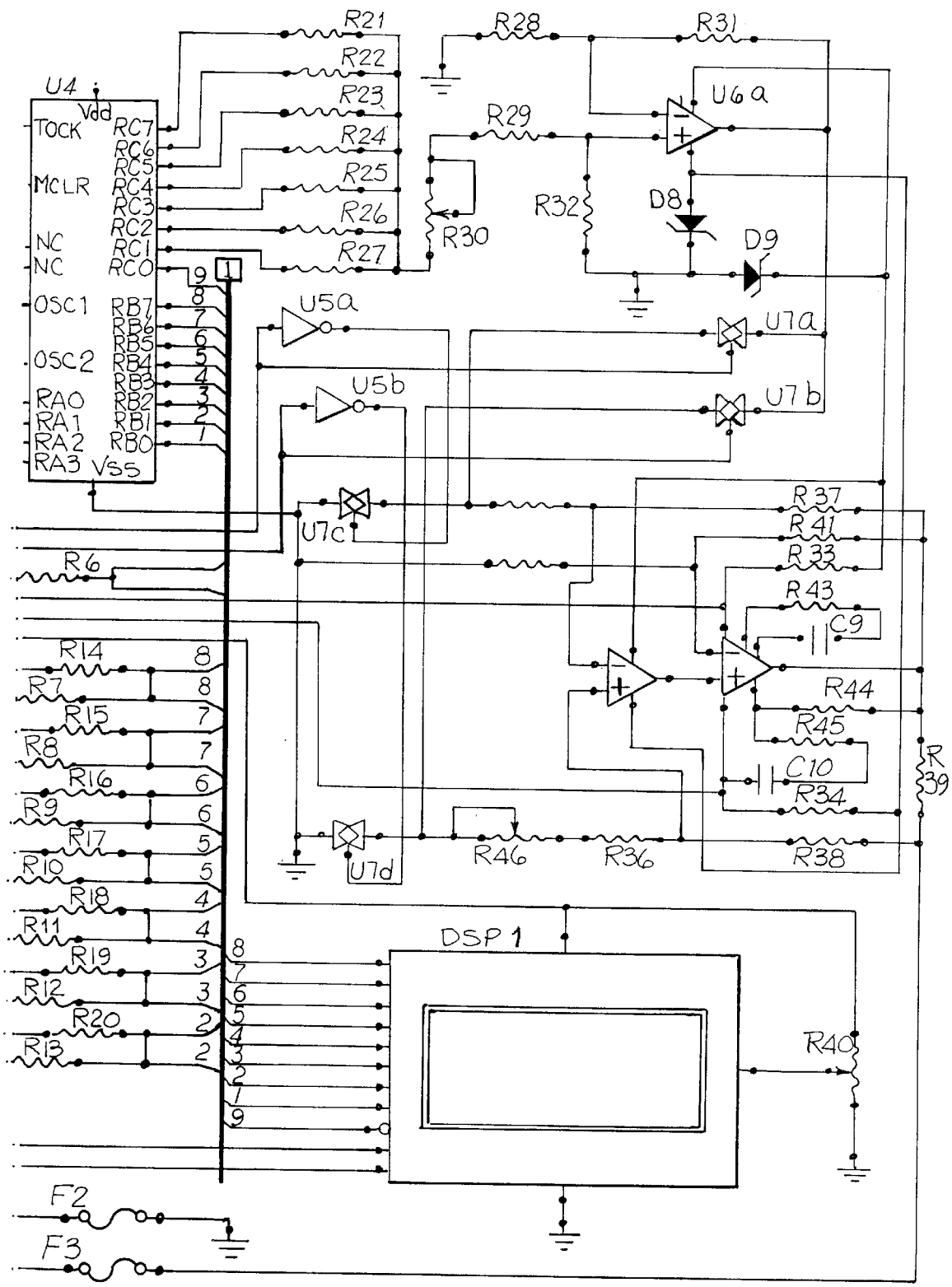
Figure 3:
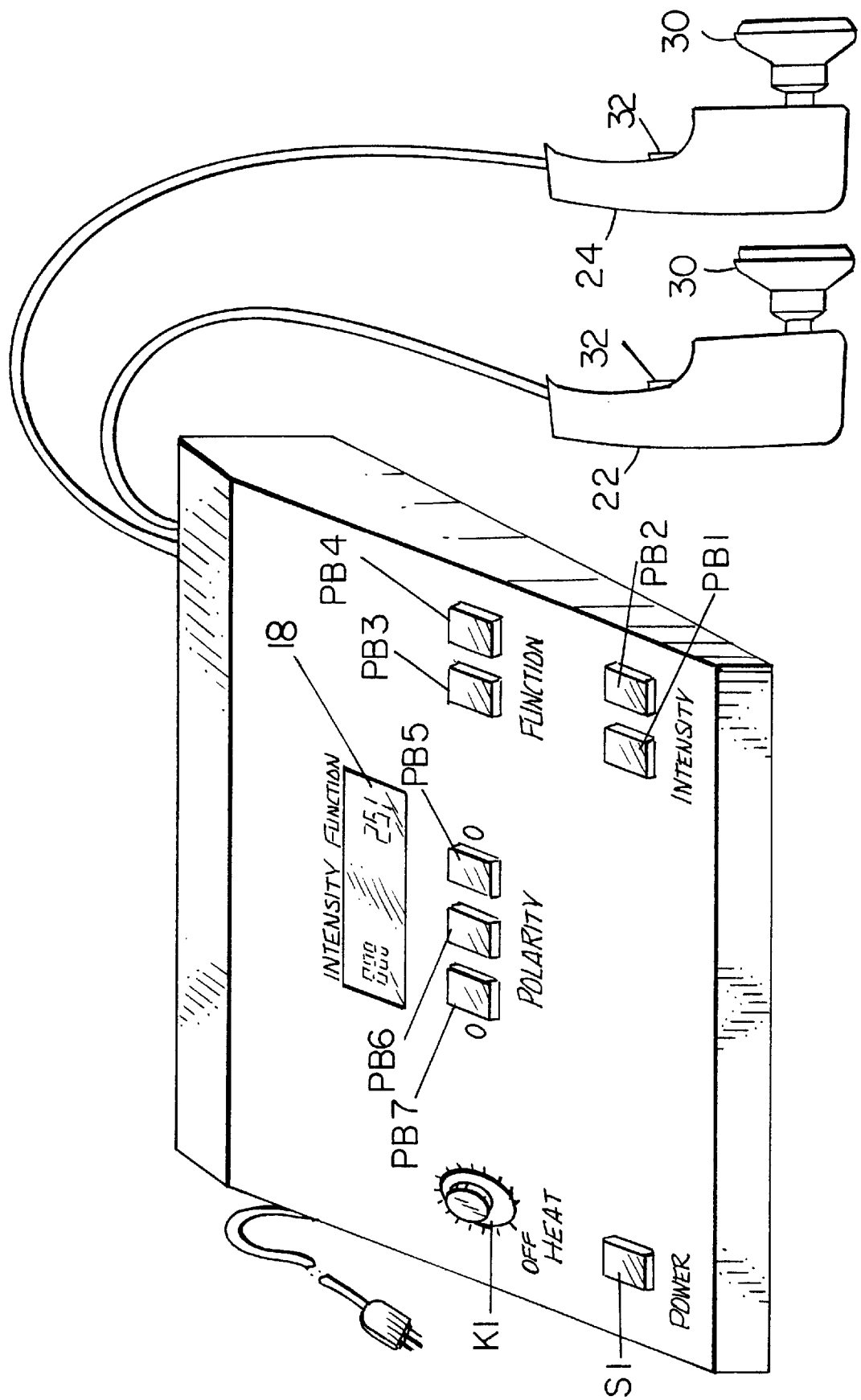
FIG. 3 is a perspective view of the apparatus of FIG. 1.

Switches 26 are individually identified in FIGS. 2 and 3 as push button switches S1, S2 and PB1 through PB7. Display 18 is identifed in FIG. 2A as display DSP1.

When turning on the power with operating switch S1, microcomputer U3 initializes so that it is ready to receive further input from one of the push-buttons. Push-button PB1 is programmed to increase the output current with each successive button press between thirteen preset intensities. The preferred preset current intensities of unit 10 range from 80 to 3400 microamps and specifically are as follows: 80, 100, 200, 400, 800, 1200, 1600, 2000, 2400, 2800, 3000, 3200, and 3400 microamperes. Push-button PB2 is programmed to decrease the output current with each successive button press through the same preset currents intensities. Similarly, push-buttons PB3 and PB4 are programmed to respectively increase and decrease the output frequency with each successive button press through a series of 7 preset fequencies which are as follows: 0.6, 15.72, 31.44, 62.88, 125.76, 251.52 and 503.4 Hz. Push-button PB5 is programmed to select positive output polarity, push-button PB6 is programmed to select bi-polar output power and push-button PB7 is programmed to select negative output polarity. The selected output current, frequency and polarity selection is displayed on the display DSP1 as identified in the schematic of FIG. 2A and as a so identified in all Figures by numeral 18. This display is an industry standard liquid crystal display and contains all the necessary circuitry to store and display the information from the microcomputer. The data inputs for the display are connected to the microcomputer register B and the control inputs are connected to the microcomputer connections identified as RA2, RA3 and RC0. Resistor R40 adjusts the display intensity.

Returning now to FIG. 2A, the microcomputer's B register connections RB0 through RB7 are also used to read out the push-button switches. This is done by lowering the RB0 terminal and reading the input on the RB1 through RB7 leads. The register C connections RC1 through RC7 are used to program the probe current while the register A connections RA0 and RA1 select the polarity as discussed above in the description for the probe driver circuit. The oscillator consists of crystal X1 and capacitors C7 and C8 along with the internal circuitry of the microcomputer.

Parts used in the circuit of unit 10 as identified in FIGS. 2 and 2A are as follows: C1, C3 and C5 are 100 uF capacitors; C2, C4 and C6 are 1 uF capacitors; C7 and C8 are 56 pF capacitors; C9 is an 18 pF capacitor; C10 is a 330 pF capacitor; D1 is a Bridge; D2, D3, D4 and D5 are 1N4001 Diodes; D6 and D7 are LED1 Diodes; D8 and D9 are 1N4744 Zener diodes; F1 is a 500 mA fuse; F2 and F3 are 10 mA fuses; P1*a*, P1*b* and S2 comprise a 500 Ohm, Rheostat; R1 and R3 are 243 Ohm, 1% resistors; R2 and R4 are 8.45 k, 1% resistors; R5 is a 220 Ohm resistor; R6 and R45 are 100 Ohm resistors; R7, R8, R9, R10, R11, R12 and R13 are 10 k resistors; R14, R15, R16, R17, R18, R19 and R20 are 100 k resistors; R21 is a 43.5 k, 1% resistor; R22 is a 34.8 k, 1% resistor; R23 is a 17.4 k, 1% resistor; R24 is a 8.66 k, 1% resistor; R25 is a 4.32 k, 1% resistor; R26 is a 3.48 k, 1% resistor; R27 is a 1.74 k, 1% resistor; R28 is a 45.3 k, 1% resistor; R29 is a 44.2 k, 1% resistor; R30 is a 5 K resistor, Cermet Trimmer [Calibrate]; R31 and R32 are 15.8 k, 1% resistors; R33 and R34 are 1 k resistors; R35 and R36 are 50 k, 0.1% resistors (*SEE NOTE BELOW); R37 and R38 are 150 k, 0.1% resistors (*SEE NOTE BELOW) *(use the sections of a resistor Network to make up these resistors) R39 is a 1.00 k, 1% resistor; R40 is a 10 k resistor Trimmer [Intensity]; R41 is a 25 k resistor; R42 is a 5 k resistor; R43 is a 2.2 K resistor; R44 is a 470 Ohm resistor; R45 is a 1 k resistor, Cermet Trimmer [Balance]; T3*b*, T3*a*, T1 are transformers, 10 to 1; T2*b* are T2*a* transformers, 3 to 1; U1 is a 78L05 voltage regulator; U2 is a variable voltage regulator, Positive, National Semiconductor, LM317HVT; U3 is a variable voltage regulator, Negative, National Semiconductor, LM337; U4 is a microcomputer, Microchip, Inc. Model No. PIC16C55; U5 is a 74HC04 hex inverter; U6(*a,b*) is a Dual Operational Amplifier, Motorola LF412C; U7(*a–d*) is a 4016 quad CMOS analog switch; U8 is an Operational Amplifier, Apex Microtechnology Corp. of Tuscon, Ariz., Model No. PA41; X1 is a 4.000 MHZ Crystal.

Operation

To use desktop unit 10 in accordance with the present invention for body toning, i.e. muscle toning and body fat reduction, one preferably begins by rubbing a body lubricant such as an ultrasound gel on the area of the body to be treated. Such a lubricant facilitates movement of probes 22, 24 on the body and also reduces any discomfort associated with use of the probes. One then turns unit 10 on as previously mentioned by pressing switch S1 so that it is in its on position. One then sets the desired frequency and current of the signal for the desired treatment to be applied to an area of the subject's body by pushing the appropriate buttons provided therefor, i.e. buttons PB1 or PB2 for respectively increasing or decreasing the current as previously described, and buttons PB3 or PB4 for respectively increasing or decreasing the frequency as also previously described. The desired polarity of the signal is then set by pushing one of buttons PB5–PB7. If heat is to be applied, knob K1 on unit 10 is turned to the desired heat setting which will heat the generally flat metallic heads of applicators 30 of each probe to the desired temperature. Applicators 30 are also capable of being vibrated to apply a vibratory massaging effect. To vibrate applicators 30, a switch 32 is provided on each probe for selecting one of two preset speed settings such as a high speed setting of about 100 Hz and a low speed setting of about 50 Hz.

As shown in FIG. 3, a current of 800 microamps and a frequency of 251 Hz have been selected to carry out one of the various body toning treatments or methods of the present invention.

The probes are now ready to be used in accordance with the method or technique of the present invention for body toning to reduce total body fat. The method involves three main steps, all of which use probes 22, 24 of the desktop unit. The first step is referred to as the muscle toning step. The second step is referred to as the fat reduction or fat implosion step, and the third step is referred to as the gliding step.

In the muscle toning step, the probes are grasped by the individual who is to perform the treatment so that he or she has a probe in each hand. The probes are then placed on an area of the subject's body (i.e. against the skin of this area) over a muscle to be toned and then moved in a manner relative to each other to either relax and/or tighten the muscle. With some muscles, toning is accomplished by relaxing and then tightening the muscle. With other muscles such as the hamstring one only relaxes the muscle and with muscles such as the abdominal muscles, one tightens the muscle.

In any event, to relax a muscle, one first places the probes against the skin about one half to one inches apart from each other and in a position over the muscle so that the electrical signal or current flowing between the probes flows through the skin and muscle located between or against the probes' heads 30. One then preferably moves the probes away from each other along the length of the muscle. Such movement of the probes away from each other has been found to lengthen the muscle and thereby relax it.

In a preferred technique of relaxing the muscle, one of the probes is held in a stationary position while the other probe is moved away from the stationary probe along the length of the muscle. The movement process is preferably done slowly so that it takes about 10 seconds on a typical muscle such as the hamstring. On some muscles it may be preferable to initially place the probes at the center or belly of the muscle, and then move the probes outwardly away from each other along the muscle toward the muscle tendons.

As previously mentioned, as this probe movement is taking place, unit 10 should be on so that an electrical signal, i.e. current flows between the probes and through the skin and muscle located between or against the probes' heads 30. In addition, prior to toning a muscle with the probes, unit 10 should be set so that the electrical signal preferably has a frequency between about 0.6 and 325 Hz and a current between about 1800 and 3200 micro amperes. A more preferred frequency and current range for muscle toning is between 125 and 280 Hz and between 2000 and 2800 micro amperes, respectively. The voltage of the signal being applied to the subject will be between 0.5 and 36 volts and will vary with the current output of the probes.

After carrying out this relaxation technique, the process is preferably repeated on an immediately adjacent area of the muscle, or an adjacent muscle, until an entire area or muscle requiring treatment is relaxed.

If a muscle requires tightening for proper toning, probes 22, 24 are preferably placed a certain distance away from each other at the ends of the muscle and then moved towards each other. This process of moving the probes towards each other again generally takes approximately 10 seconds depending on the muscle being treated, after which the process is repeated on an adjacent area of the muscle until the entire area or muscle is treated.

While the foregoing muscle toning step is preferably the first step of the body toning method, it may be performed as a separate treatment by itself, i.e. as simply a muscle relaxation or tightening technique. In addition, it is not necessary to carry out the muscle toning step with the following fat reduction step which may also be carried out as a separate treatment by itself.

The next step of the body toning method of the present invention is, as indicated above, the fat reduction or implosion step. Prior to carrying out this step, the probes' current output should be adjusted, usually increased, to somewhere between about 2000 and 3600 microamps. The frequency of the probes' signal should also be adjusted so that it is somewhere between approximately 15 and 60 Hz.

After adjusting the signal of the probes as indicated above, the technician or operator begins the fat reduction step by squeezing or pinching approximately an inch of fatty tissue between the probes' heads 30 for approximately four seconds. The procedure is then repeated on adjacent areas until the entire area requiring treatment is treated.

While it is uncertain as to exactly what takes place when the fatty tissue cells are squeezed as indicated above, it is believed that the squeezing and application of the electrical signal actually ruptures, or at least breaks down the fat cells in the treated area, thereby releasing the contents of the fat cells into the body fluid where it is ultimately excreted from the body. This breaking down or rupturing of the fat cells is also referred to herein as implosion of the fat cells.

The probes' heads 30 should also be vibrated during the fat reduction step. Probe vibration has been found to mask any discomfort associated with the relatively high levels of current applied during the fat implosion step, thereby allowing the application of higher currents, i.e. currents which would otherwise be painful to the subject.

As mentioned previously, the metallic heads of the probes are preferably provided with two speed vibrators which vibrate at two preset speeds of 50 and 100 Hz. A commercially available vibrator having the aforementioned vibratory speeds which was modified in accordance with the electronics of FIG. 2 to pass current through the probes, is available from the Wahl Clipper Corporation of Sterling, Ill., model number 4196-Type.

The probes are also preferably provided with circuitry for heating their metallic heads 30 so that a treated area may be heated as it is vibrated and stimulated with the probes. The application of heat generally makes the process more pleasurable and less painful to subjects. It also tends to improve the subject's circulatory system by opening up superficial capillaries to enhance vascular flow, which is believed to have the advantage of discouraging or inhibiting fat cell build up in areas of restricted circulation which are often produced by tight or restrictive clothing.

In any event, after completing the fat implosion step, the aforementioned gliding step should be immediately carried out. Before doing so, however, the signal generated by the probes should again be adjusted so that its current is between about 1600 and 2400 microamps and its frequency between about 125 and 600 Hz.

The gliding step involves moving, actually gliding, of the probes in spaced unison over the plurality of adjacent fatty areas which were imploded during the preceding fat implosion or reduction step. Spaced unison as used herein means that the probes are preferably spaced about one half to one inch apart from each other as they are glided or moved together in unison over the treated area. The gliding process is preferably carried out slowly and usually takes about ten seconds per stroke, and is repeated until the entire area is covered. The gliding process can also be thought of as a sculpting process in that the stroking movement is somewhat similar to that made by in sculpturing.

As with the fat reduction or implosion step, exactly what occurs physiologically during the gliding step is unknown. However, it is believed that gliding somehow facilitates absorption of the ruptured or broken down fat cell contents into the body fluid, thereby facilitating their excretion from the body.

The foregoing body toning treatment should be repeated twice a week for at least three weeks or until satisfactory results are obtained.

The current, polarity and frequency of the signal may be occasionally adjusted to prevent the muscle or fatty tissue from acclimating or habitualizing to any frequently used signal.

This invention has been described in detail with reference to particular embodiments thereof, but it will be understood that various other modifications can be effected within the spirit and scope of this invention.

What is claimed is:

1. A body toning method comprising the steps of:

energizing a pair of electrodes so that they are capable of applying a first electrical signal to a subject's body for rupturing fat cells;

squeezing a fatty area of a subject's body with the energized pair of electrodes to apply the first electrical signal to the fatty area and rupture fat cells in the fatty area, thereby releasing the contents of the ruptured fat cells into the body fluid which facilitates excretion of the contents from the body; and, periodically repeating the foregoing steps to reduce the fat content of the fatty area.

2. A body toning method as claimed in claim 1 wherein said pair of electrodes are energized so that the first electrical signal has a frequency between 15 and 60 Hz and a current between 2,000 and 3,600 micro amperes.

3. A body toning method as claimed in claim 1 further comprising:

adjusting the energization of the electrodes so that they are capable of applying a second electrical signal which is different than the first electrical signal;

gliding the electrodes generating the second signal in spaced unison over the fatty area to facilitate excretion of the released fat cell contents from the body.

4. A body toning method as claimed in claim 3 wherein said pair of electrodes are energized so that the second electrical signal has a frequency between 125 and 600 Hz and a current between 1,600 and 2,400 microamps.

5. A body toning method as claimed in claim 1 further comprising mechanically vibrating said electrodes so that the first fatty area is vibrated as it is squeezed with the energized electrodes.

6. A body toning method as claimed in claim 1 further comprising heating said electrodes so that the first fatty area is heated as it is squeezed with the energized electrodes.

7. A body toning method as claimed in claim 1 further comprising mechanically vibrating and heating said electrodes so that the first fatty area is vibrated and heated as it is squeezed with the energized electrodes.

8. A body toning method as claimed in claim 7 wherein during said step of mechanically vibrating and heating said electrodes the electrodes are mechanically vibrated at a frequency between 50 and 100 Hz and heated to a temperature which the subject can tolerate.

9. A body toning method as claimed in claim 1 wherein said step of squeezing the fatty area is carried out for about 4 seconds.

10. A body toning method as claimed in claim 1 wherein said pair of electrodes are energized so that the signal is a square wave.

11. A body toning method as claimed in claim 1 wherein said step of periodically repeating is carried out by repeating the energizing and squeezing steps at least twice a week for three weeks.

12. A body toning method as claimed in claim 1 wherein said step of periodically repeating is carried out by repeating the energizing and squeezing steps at least twice a week until satisfactory results are obtained.

13. A body toning method as claimed in claim 1 wherein said pair of electrodes are energized so that the polarity of the signal is selected from a member of the group consisting of positive, negative and bipolar.

14. A body toning method as claimed in claim 1 wherein the first electrical signal has a frequency and wherein the method further comprises the step of periodically altering the frequency of the first electrical signal.

15. A body toning method as claimed in claim 1 wherein the first electrical signal has a polarity and wherein the method further comprises the step of periodically altering the polarity of the first electrical signal.

16. A body toning method as claimed in claim 1 wherein the first electrical signal has a predetermined current and wherein the method further comprises the step of periodically altering the current of the first electrical signal.

17. A body toning method as claimed in claim 1 wherein the electrodes are of the vibratory type having generally flat metallic heads.

18. A body toning method comprising the steps of:
energizing a pair of vibratory electrodes so that they are capable of applying a first electrical signal having a frequency between 15 and 60 Hz, a current between 2,000 and 3,600 micro amperes and a voltage between 20 and 36 volts;

sequentially squeezing a plurality of adjacent fatty areas on a subject's body with said energized pair of electrodes so as to rupture fat cells in the plurality of fatty areas, the rupturing of which releases the contents of the ruptured fat cells into the body fluid where it is excreted from the body;

adjusting the energization of the electrodes so that they generate a second electrical signal having a frequency between 125 and 600 Hz, a current between 1,600 and 2,400 microamps and a voltage between 16 and 24 volts;

gliding the electrodes generating the second signal in spaced unison over the plurality of adjacent fatty areas to facilitate excretion of the released fat cell contents from the body; and, periodically repeating the foregoing steps to reduce the fat content of the plurality of fatty areas.

19. A body toning method as claimed in claim 18 wherein the spacing of the electrodes is between about 0.5 to 2 inches as they are moved in spaced unison during the gliding step.

20. A body toning method comprising the steps of:
energizing a pair of electrodes so that they are capable of applying a first electrical signal which is sufficient to rupture fat cells;

squeezing a fatty area of a subject's body with said energized pair of electrodes to break down the fat cells in the fatty area so that the contents of the ruptured fat cells are released into the body fluid;

adjusting the energization of the electrodes so that they are capable of applying a second electrical signal for facilitating absorption of the released fat cell contents into the body fluid which facilitates its excretion from the body;

after adjusting the energization of the electrodes, gliding the electrodes over the fatty area to facilitate absorption of the released fat cell contents into the body fluid which facilitates its excretion from the body; and, periodically repeating the foregoing steps to reduce the fat content of the fatty area.

21. A body toning apparatus comprising:
a pair of hand held devices, each of which has an electrode including means for vibrating said electrode;

energizing means for energizing said electrodes so that they are capable of applying an electrical signal having a selected frequency between about 0.6 and 505 Hz, a selected current between about 50 and 3400 microamps and a voltage between about 0.5 and 34 volts when said electrodes are proximate each other and in contact with a subject's body; and, means for selecting the signal's frequency and current.

22. A body toning apparatus as recited in claim 21 further comprising means for displaying the selected frequency and current.

* * * * *